United States Patent [19]

Laurin et al.

[11] Patent Number: 4,603,152

[45] Date of Patent: Jul. 29, 1986

[54] ANTIMICROBIAL COMPOSITIONS

[75] Inventors: Dean Laurin, Lake Zurich; James Stupar, Crystal Lake, both of Ill.

[73] Assignee: Baxter Travenol Laboratories, Inc., Deerfield, Ill.

[21] Appl. No.: 655,762

[22] Filed: Oct. 1, 1984

Related U.S. Application Data

[63] Continuation-in-part of Ser. No. 439,506, Nov. 5, 1982.

[51] Int. Cl.⁴ .............................................. A61M 25/00
[52] U.S. Cl. ................... 604/265; 106/15.05; 106/16; 604/265; 3/1; 424/83; 424/132; 424/131; 523/122
[58] Field of Search ............... 106/15.05, 16; 523/122; 604/265

[56] References Cited

U.S. PATENT DOCUMENTS

| | | | |
|---|---|---|---|
| 861,231 | 7/1907 | Clarke | 128/335.5 |
| 1,767,073 | 6/1930 | Ingold | 604/179 |
| 2,653,893 | 9/1953 | Romans | 167/14 |
| 2,689,809 | 9/1954 | Fessler | 117/138.5 |
| 2,791,518 | 5/1957 | Stokes | 117/120 |
| 2,813,056 | 11/1957 | Davis et al. | 167/14 |
| 2,947,282 | 8/1960 | Brown | 119/14.47 |
| 3,350,265 | 10/1967 | Rubinstein et al. | 167/38.6 |
| 3,434,869 | 3/1969 | Davidson | 117/94 |
| 3,598,127 | 8/1971 | Wepsic | 128/349 |
| 3,695,921 | 8/1968 | Shepherd et al. | 427/2 |
| 3,830,908 | 8/1974 | Klippel et al. | 424/28 |
| 3,906,958 | 9/1975 | Knox | 128/349 |
| 3,975,350 | 8/1976 | Hudgin et al. | 260/30 |
| 4,054,139 | 10/1977 | Crossley | 604/265 |
| 4,284,444 | 8/1981 | Bernstein et al. | 156/60 |
| 4,483,688 | 11/1984 | Akiyama | 604/265 |
| 4,515,593 | 5/1985 | Norton | 604/265 |

*Primary Examiner*—Maurice J. Welsh
*Assistant Examiner*—M. L. Moore
*Attorney, Agent, or Firm*—Paul C. Flattery; John A. Caruso; Kay H. Pierce

[57] ABSTRACT

Antimicrobial compositions finding particular utility for coating access systems, lead devices including shunts, cannulae, catheters, catheter adapters, wires and other solid or hollow tubular devices used for a variety of medical purposes is provided. The composition comprises a material selected from the group consisting of acrylonitrile-butadiene-styrene copolymers, polyvinyl chloride, mixtures thereof, polyesters, polyurethanes, styrene-block copolymers, natural and synthetic rubbers, polycarbonates, nylon and silicone rubber mixed with an oligodynamic material consisting essentially of compounds of physiological, antimicrobial metals.

19 Claims, 3 Drawing Figures

ANTIMICROBIAL COMPOSITIONS

RELATED APPLICATIONS

This application is a continuation in part of application filed Nov. 5, 1982 bearing Ser. No. 439,506.

FIELD OF THE INVENTION

This invention relates to compositions useful in making medical devices and useful in providing antimicrobial coatings on medical devices. The invention particularly relates to antimicrobial compositions useful as coatings for medical connection devices and for making medical connection devices which are susceptible to touch contamination. These compositions are also useful as antimicrobial coatings for access systems and lead devices (for example, shunts, cannulae, catheters, wires, enteral feeding tubes, endotracheal tubes, percutaneous devices and other solid or hollow tubular devices) used for a variety of medical purposes. In addition, the compositions may be used as antimicrobial coatings for wound coverings or in the manufacture of thin, flexible, skin-like wound coverings.

BACKGROUND OF THE INVENTION

Indwelling urethral catheterization is performed in approximately 10 to 15 percent of hospitalized patients. About 25 percent of these patients contract bacterial infections of the urinary tract. Two studies of note are, Garibaldi, R. A.; Burke, J. P.; Dickman, M. L.; and Smith, C. B., "Factors Predisposing to Bacteriuria During Indwelling Urethral Cathiterization". *New Engl. J. Med.*, 291:215, 1974 and Kunin, C. M. and McCormack, R. C., "Prevention of Catheter—Induced Urinary—Tract Infections by Sterile Closed Drainage". *New Engl. J. Med.*, 274:1155, 1966.

The incidence of catheter—induced urinary tract infection still remains a problem despite various prophylactic measures that have been tried. Attempts to reduce the incidence of urinary tract infections have included the application of antibiotic ointments or other bactericidal agents to the surface of the catheter, frequent bladder irrigation with concommittant prophylactic administration of antibiotics, or inhibition of the growth of bacteria in urine drainage containers. See, Akiyama, H. and Okamoto, S., "Prophylaxis of Indwelling Urethral Catheter Infection: Clinical Experience with a Modified Foley Catheter and Drainage System". *The Journal of Urology*, 121:40, 1979. U.S. Pat. No. 4,054,139, Oligodynamic Catheter, to Crossley, teaches a catheter, percutaneous lead device, or the like, which comprises an oligodynamic agent such as metallic silver or its compounds, alone or in association with other heavy metals such as gold, for the purpose of reducing infection associated with these devices.

It would be desirable to provide compositions useful as coatings for urinary catheters, lead devices, medical connections susceptible to touch contamination and the like, and compositions useful as a meterial for making these various devices, whereby the proliferation of bacteria thereon or in relatively close proximity thereto is inhibited. Inhibiting the proliferation of bacteria on urinary catheters and catheter adapter connections would reduce the risk of urinary tract infection caused by bacteria accessing the urinary tract at these sites. It also would be desirable for the compositions to be easily applied as coatings on presently existing medical connections and devices. A desirable characteristic of such a composition would be an antimicrobial effect which is long lasting without being physiologically incompatible with nearby tissue.

DESCRIPTION OF THE INVENTION

In accordance with this invention, antimicrobial compositions are provided which find particular utility as coatings which inhibit the proliferation of bacteria near the surface or urinary catheters and the connection between the catheter and the drainage tube, namely, the catheter/catheter adapter junction site. The antimicrobial coating on the catheter inhibits the proliferation of bacteria in the area between the catheter and the walls of the urethra, and the antibacterial coating on the catheter adapter inhibits the proliferation of bacteria in the closed area connecting the catheter and the catheter adapter.

Catheters implanted in patients undergoing continuous ambulatory peritoneal dialysis also can be coated with an antimicrobial composition of this invention. An antimicrobial composition of this invention can be applied as a coating to medical shunts, cannulae, catheters, wires and other solid or hollow tubular devices used for medical purposes.

Preferably, the coating using an antimicrobial composition is prepared by mixing a suitable resin and a compound of a physiological, antimicrobial metal in an appropriate solvent for the resin. The solvent should not adversely effect the activity of the metal compound as an antimicrobial agent. The coating can be applied to a medical device by dipping in the mixture of resin, solvent, and physiological, antimicrobial metal compound and thereafter allowing the solvent to evaporate. Both inside and outside surfaces may be coated. Alternatively, the medical articles may be sprayed with the mixture and the solvent allowed to evaporate. Where appropriate, particularly with a latex rubber resin, a volatile liquid carrier may be used with the resin dispersed in the volatile liquid. An article may be dipped or sprayed with this preparation. Upon evaporation of the volatile liquid and curing of the resin a coating for the article is provided.

Indeed, articles can be made from a composition of a suitable resin and a compound of physiological, antimicrobial metal by molding the composition to form the article.

The resins used in formulating the mixture include, for example, acrylonitrile-butadiene-styrene copolymer, rigid polyvinyl chloride, curable silicones, alkoxy cured RTV silicone rubber, acetoxy cured RTV silicone rubber, polyesters, rubber latexes (e.g., natural or synthetic polyisoprene), polyurethanes, styrene-block copolymers (e.g., Kraton-D and Kraton-G, manufactured by Shell), ethylene copolymers (e.g., vinyl acetate, ethyl acrylate, or mixtures thereof), ethylene copolymers of maleic anhydride, acrylic acid or both, polycarbonates, nylons, and polymethyl methacrylate.

Into a mixture of resin and solvent is added a quantity of physiological, antimicrobial metal compound. Alternatively, a quantity of physiological, antimicrobial metal compound may be mixed with a resin for direct molding of an article. Physiological, antimicrobial metals are meant to include the precious metals, such as silver, gold and platinum, and copper and zinc. Physiological, antimicrobial metal compounds used herein include oxides and salts of preferably silver and also gold, for example: silver acetate, silver benzoate, silver carbonate, silver citrate, silver chloride, silver iodide, silver nitrate, silver oxide, silver sulfa diazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used.

Preferred physiological, antimicrobial metal compounds used in this invention are silver acetate, silver oxide, silver sulfate, gold chloride and a combination of silver oxide and gold chloride. Preferred quantities of physiological, antimicrobial metal compound are those sufficient to produce, within a 24 hour period, a solution of at least $10^{-6}$ molar concentration of metal ion concentration in a stagnant film of liquid on contact with a surface of an article made from a composition of this invention or an article coated with a composition of this invention. The particles of the silver compounds are sufficiently able to be extracted to form a zone of inhibition to prevent and kill bacteria growth. The zone of inhibition being defined by metal ion concentration as discussed above.

BRIEF DESCRIPTION OF THE DRAWINGS

For a more complete understanding of this invention, reference should now be had to the embodiments illustrated in greater detail in the accompanying drawings.

In the drawings.

DETAILED DESCRIPTION OF THE DRAWINGS

Figure 1:
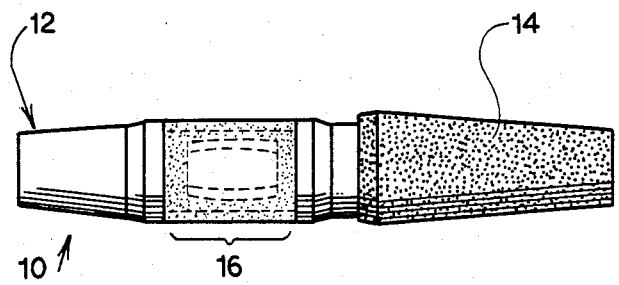
FIG. 1 is an elevational view of a catheter adapter showing one end coated with an antimicrobial composition of this invention.

Turning now to the drawings, FIG. 1 shows a conventional catheter adapter 10 after it has been coated with an antimicrobial composition of this invention. Catheter adapter 10 has drainage tube end 12, catheter end 14, and injection site 16.

Catheter end 14 is spray coated or dip coated with an antimicrobial composition of this invention. The shaded portion of catheter end 14 is illustrative of the coating.

Figure 2:
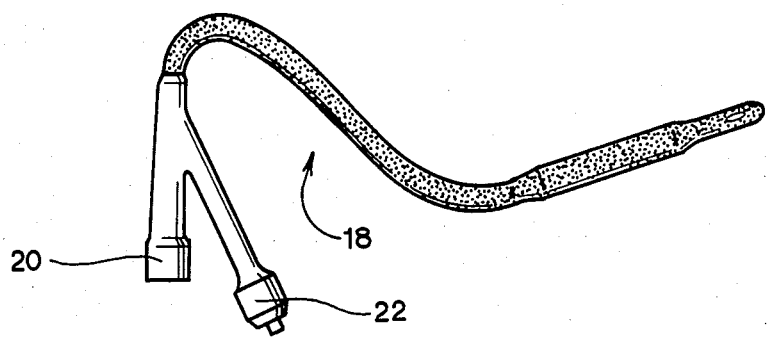
FIG. 2 is an elevational view of a Foley catheter showing the portion of the catheter typically inserted into the urethra, coated with an antimicrobial composition of this invention.

FIG. 2 shows urinary catheter 18. Catheter 18 has drainage connection 20 and inflation connection 22 for inflating the catheter balloon.

The shaded portion of catheter 18 illustrates the area coated by an antimicrobial composition of this invention. Typically, this coating will be applied to that portion of catheter 18 which resides in the urethra of a patient.

Figure 3:
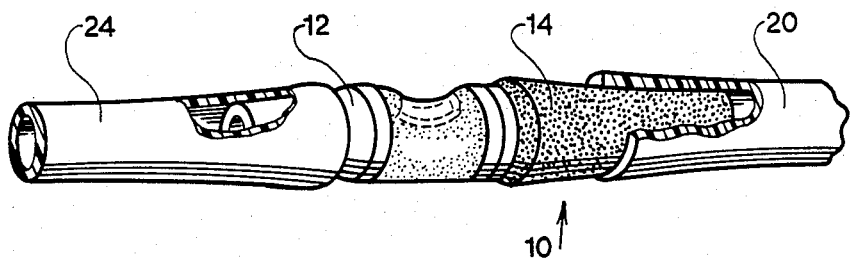
FIG. 3 is a perspective view of the catheter adapter of this invention shown connecting a urinary drainage tube and a catheter.

A typical connection of catheter adapter 10 is illustrated in FIG. 3. Catheter adapter 10 has the coated catheter end 14 connected to drainage connection 20 to the catheter. Drainage tube end 12 is connected to drainage tube 24 to complete the connection. Drainage tube 24 drains into a urinary drainage bag (not shown).

The risk of touch contamination of catheter end 14 is reduced by coating catheter end 14 of catheter 10 with an antimicrobial composition of the present invention. Reducing the risk of touch contamination of catheter end 14 reduces the risk of subsequent urinary tract infection caused by a contaminated catheter adapter.

The antimicrobial composition coating catheter 18 inhibits the proliferation and migration of bacteria in a stagnant film between the coated catheter walls and the walls of the urethra. By inhibiting the proliferation and migration of bacteria through this route, subsequent urinary tract infection caused by such proliferation and migration of bacteria is reduced.

Design characteristics of the antimicrobial coating are dicatated by the medical devices it will coat. Therefore, careful thought must be given to the use of the medical device. For example, a catheter's antimicrobial coating design characteristics are different from a catheter adapter/rigid connecters antimicrobial coating design characteristics which are different from a short term, flexible poly vinyl chloride catheter's antimicrobial coating design characteristics.

The design characteristics are varied by particle size of the antimicrobial metal compounds, dielectric constant of the resin portion of the coating/binder and of course, concentration, which speaks for itself. Particle size affects dosage and duration. Normally larger particle size means higher initial dose and short duration with small particle size meaning lower initial dose and longer duration.

The dielectric constant of the binder/coating plays an important role in design characteristics by effecting initial dosage and duration. Binder coating materials with high dielectric constants lead to discreetly dissolved particles within the coating itself. This means, particles are on the surface as well as in the binder/coating. Particles need a route to the surface to effect a zone of inhibition, if buried they are ineffective. Therefore, materials with high dielectric constants provide an initial high dose of short duration because the surface particles form the initial high dose but the buried particles have no path to the surface to effect a longer duration.

Binder/coating materials with low dielectric constants allow particles to form chain like structure between themselves. This allows the surface particles to dissolve to create an initial dose, but also provides a pathway for interior particles to come to the surface to continue to maintain the desired zone of inhibition.

In a catheter, the rate of release/control of delivery needs to be such that the optimal zone of inhibition is created and maintained for the longest duration possible. Large particle size offers an initial high dosage but, one must bear in mind that the catheter is in intimate human tissue contact. Large particles are rougher thereby leading to tissue irritation. Therefore, smaller particle size should be choosen for longer duration and less irritation. As discussed above, a binder/coating material should be choosen with a low dielectric constant to provide a longer duration by providing a chain like structure for particles to reach the surface and form the zone of inhibition. Therefore, in a silicone rubber Foley catheter, a low dielectric constant coating/binder material combined with small particle size (submicron) and a concentration from 0.15%–70% of the antimicrobial compound (depending on use) will give a desired concentration for the zone of inhibition with maximum duration and minimal human tissue irritation.

For a catheter adapter/rigid connecter where there is no human tissue contact and an initial high dose rate may be needed due to inadvertent touch contamination. The design characteristics differ from that of a catheter. Concentration of the antimicrobial metal compound, from 0.15%–70% will again be able to be varied as desired.

A flexible PVC catheter is primarily used as a short term catheter and is of low cost. In one embodiment the binder/coating material is selected to lead to high dosage rate of short duration with small particle size (due to human tissue contact). The concentration of the antimicrobial compound is to be maxmized for a high rate, short duration use.

The examples below are offered for illustrative purposes only and are not intended to limit the scope of the invention of this application, which is as defined in the claims below.

EXAMPLE 1

A mixture was made of 50 milliliters of methylene chloride, 5 grams of acrylonitrile-butadiene-styrene copolymer (LUSTRAN 240-29, a trademark of the Monsanto Company), and 1.2 grams of silver oxide powder. The mixture was stirred for approximately one hour. A polyvinyl chloride catheter adapter, used to connect a urinary catheter and drainage tubing for a urinary drainage connector, was coated on the exterior and the interior by dipping the connector into the mixture. Upon evaporation of the solvent, an antimicrobial coating remained bonded to the catheter adapter. Catheter adapters can also be sprayed with the mixture.

EXAMPLE 2

A mixture was made by combining 50 milliliters of tetrahydrofuran, 5 grams of polyvinyl chloride (Alpha Plastics and Chemicals, clear rigid vinyl 2212/7-118), and 1.2 grams of silver oxide powder. The mixture was stirred for about one hour.

Vinyl compatible catheter adapters may be either dip coated or spray coated with this mixture. By dip coating the catheter adapter, the exterior and interior surfaces may be conveniently coated. Upon evaporation of the solvent, tetrahydrofuran, an antimicrobial coating will remain bonded to the device.

EXAMPLE 3

Equivalent results may be obtained when a mixture is made by combining 25 milliliters of tetrahydrofuran, 25 milliliters of methylene chloride, 2.5 grams of acrylonitrile-butadiene-styrene copolymer (LUSTRAN 240-29), 2.5 grams of polyvinyl chloride (Alpha Plastics and Chemicals, clear rigid vinyl 2212/7-118), and 1.2 grams of silver oxide powder. The mixture may be stirred for about one hour.

A catheter adapter may be either dip coated or spray coated with this mixture. Upon evaporation of the solvents, an antimicrobial coating will remain bonded to the device.

EXAMPLE 4

A mixture was made by combining 10 milliliters of alkoxy curing RTV rubber, 65 milliliters of FREON TF solvent (FREON is a trademark of E. I. du pont de Nemours & Co.), and 5 grams of silver oxide powder. The mixture was stirred for about one hour.

A silicone rubber Foley catheter was dipped into this mixture and upon evaporation of the solvent and curing of the RTV, a flexible, antimicrobial coating on the interior and exterior surfaces of the silicone rubber catheter was provided. The coating adhered well to the catheter. Spray coating of the catheter is a viable alternative. Further, zones of inhibition were formed which proved to be effective and safe for more than 12 days.

EXAMPLE 5

A mixture was made by combining 100 milliliters of tetrahydrofuran, 5 grams of acrylonitrile-butadiene-styrene copolymer (LUSTRAN 240-29), and 1 gram of silver acetate. The mixture was stirred for about one hour. Acrylonitrile-butadiene-styrene compatible devices may be spray or dip coated with the mixture. Upon evaporation of the solvent, an antimicrobial coating will remain on the device.

EXAMPLE 6

Equivalent results may be obtained when a mixture is made by combining 100 milliliters of methylene chloride, 5 grams of acrylonitrile-butadiene-styrene copolymer (LUSTRAN 240-29), and 1 gram of silver sulfate. The mixture may be stirred for about one hour. Acrylonitrile-butadiene-styrene compatible devices may be spray or dip coated with the mixture. Upon evaporation of the solvent, an antimicrobial coating will remain on the device.

EXAMPLE 7

Equivalent results may be obtained when a mixture is made by combining 50 milliliters of tetrahydrofuran, 5 grams of polyvinyl chloride (Alph Plastics and Chemicals, clear rigid vinyl 2212/6-118), and 1.2 grams of gold chloride powder. The mixture may be stirred for about one hour. Polyvinyl chloride compatible devices may be spray or dip coated with the mixture. Upon evaporation of the solvent, an antimicrobial coating will remain on the device.

EXAMPLE 8

Equivalent results may be obtained when a mixture is made by combining 25 milliliters of tetrahydrofuran, 25 milliliters of methylene chloride, 2.5 grams of acrylonitrile-butadiene-styrene copolymer (LUSTRAN 240-29), 2.5 grams of polyvinyl chloride (Alpha Plastics and Chemicals, clear rigid vinyl 2212/7-118), and 1.2 grams of gold chloride powder. The mixture may be stirred for about one hour. Devices may be either dip coated or spray coated with this mixture. Upon evaporation of the solvents, an antimicrobial coating remains bonded to the device.

EXAMPLE 9

Equivalent results may be obtained when a mixture is made by combining 10 milliliters of alkoxy curing RTV, 65 milliliters of FREON TF solvent and 5 grams of gold chloride powder. The mixture may be stirred for about one hour.

A silicone rubber Foley catheter or other silicone rubber medical device may be dipped into this mixture and upon evaporation of the solvent and curing of the RTV, a flexible, antimicrobial coating for the silicone rubber catheter will be provided. Spray coating of the catheter is also a viable alternative.

EXAMPLE 10

Equivalent results may be obtained when a mixture is made by combining 50 milliliters of tetrahydrofuran, 5 grams of polyvinyl chloride (Alpha Plastics and Chemicals, clear rigid vinyl 2212/7-118), 1.2 grams of silver oxide powder, and 0.1 gram of gold chloride powder. The mixture may be stirred for about one hour.

Vinyl compatible catheter adapters or other medical devices may be either dip coated or spray coated with this mixture. Upon evaporation of the solvent, tetrahydrofuran, an antimicrobial coating will remain on the device.

EXAMPLE 11

Equivalent results may be obtained when a mixture is made by combining 25 milliliters of tetrahydrofuran, 25 milliliters of methylene chloride, 2.5 grams of acrylonitrile-butadiene-styrene copolymer (LUSTRAN 240-29), 2.5 grams of polyvinyl chloride (Alpha Plastics and Chemicals, clear rigid vinyl 2212/7-118), 1.2 grams of silver oxide powder, and 0.1 gram of gold chloride powder. The mixture may be stirred for about one hour. Devices may be either dip coated or spray coated with this mixture. Upon evaporation of the solvents, an antimicrobial coating will remain on the device.

EXAMPLE 12

Equivalent results may be obtained when a mixture is made by combining 10 milliliters of alkoxy curing RTV, 65 milliliters of FREON TF solvent, 5 grams of silver oxide powder, and 0.5 gram of gold chloride powder. The mixture may be stirred for about one hour.

A silicone rubber Foley catheter or other silicone rubber medical device may be dipped into this mixture and upon evaporation of the solvent and curing of the RTV, a flexible, antimicrobial coating for the silicone rubber catheter is provided. Spray coating of the catheter is also an alternative application means.

EXAMPLE 13

Equivalent results may be obtained when a mixture is made by combining 100 milliliters of natural rubber latex with 10 grams of silver oxide powder. The mixture may be stirred until the silver oxide is dispersed. Cured latex rubber devices may be dip coated with this mixture. Upon evaporation of the volatile liquid carrier and curing of the coating mixture, an antimicrobial coating having high elastomeric characteristics will remain adhered to the device.

EXAMPLE 14

Equivalent results may be obtained when a mixture is made by combining 50 milliliters of methylene chloride, 5 grams of acrylonitrile-butadiene-styrene copolymer (LUSTRAN 240-29), and 1.2 grams of copper oxide powder. The mixture may be stirred for about one hour. A catheter adapter may be either dip coated or spray coated with this mixture. Upon evaporation of the solvent, an antimicrobial coating will remain bonded to the device.

EXAMPLE 15

Equivalent results may be obtained when a mixture is made by combining 50 milliliters of methylene chloride, 5 grams of acrylonitrile-butadiene-styrene copolymer (LUSTRAN 240-29), and 1.2 grams of zinc oxide powder. The mixture may be stirred for about one hour. A catheter adapter may be either dip coated or spray coated with this mixture. Upon evaporation of the solvent, an antimicrobial coating will remain bonded to the device.

EXAMPLE 16

A smooth, colorless coating was made by mixing 5.4 grams of silver sulfadiazine, 102 grams of alkoxy curing RTV rubber and 420 milliliters of FREON TF solvent (FREON is a trademark of E. I. dupont de Nemours & Company). The mixture was agitated for ten minutes to disperse the solids.

A silicone rubber foley catheter was dipped into the mixture and upon evaporation of the solvent and curing of the RTV a flexible, antimicrobial coating was formed.

EXAMPLE 17

EXAMPLE 17

Mixtures were made by first adding 0.85 grams, then 1.7 grams, then 2.55 grams, then 3.4 grams and finally 4.25 grams into 350 milliliters of FREON TF solvent (FREON is a trademark of E. I. dupont de Nemours & Company) and 85 grams of alkoxy curing RTV rubber.

A silicone rubber foley catheter was dipped into the mixture removed, drained and an dried at room temperature. A smooth, strong, adherent coating was formed even after catheter stretching by 50%. Further, zones of inhibition were formed which proved to be effective and safe for more then 12 days.

What is claimed is:

1. An antimicrobial composition comprising:
   30 to 85 percent by weight of a binder consisting essentially of a material selected from the group consisting of acrylonitrile-butadiene-styrene copolymers, polyvinyl chloride, mixtures thereof, polyesters polyurethanes, styrene-block copolymers, natural and synthetic rubbers, polycarbonates, nylon and silicone rubber; and
   15 to 70 percent by weight of an antimicrobial agent selected from the group consisting of compounds of antimicrobial metals and mixtures thereof that are physiologically compatible with human tissue, said binder having a sufficiently low dielectric constant so as to allow said antimicrobial agent to form a chain-like structure to create an initial dose of antimicrobial action upon first use by allowing antimicrobial ions on a surface of said composition to dissolve, said chain-like structure providing a pathway in said binder to allow interior antimicrobial ions in said composition to come to said surface of said composition to provide subsequent doses of antimicrobial action.

2. The antimicrobial composition of claim 1 in which said mixtures of acrylonitrile-butadiene-styrene copolymers and polyvinyl chloride consist of 25 to 75 percent by weight of acrylonitrile-butadiene-styrene copolymers and 25 to 75 percent by weight of polyvinyl chloride.

3. The antimicrobial composition of claim 1 in which said antimicrobial agent is selected from the group consisting of oxides and salts of silver and gold.

4. The antimicrobial composition of claim 1 in which said antimicrobial agent is selected from the group consisting of silver compounds.

5. The antimicrobial composition of claim 4 in which said antimicrobial agent is silver oxide.

6. The antimicrobial composition of claim 5 wherein said zone of inhibition forms, in 24 hours, a solution of at least $10^{-6}$ molar concentration of silver ion concentration in a stagnant film of urine in contact with said surface.

7. An antimicrobial composition for coating articles comprising:
- 30 to 85 percent by weight of a binder;
- 15 to 70 percent by weight of an antimicrobial agent selected from the group consisting essentially of silver compounds, silver oxides and mixtures thereof, said binder having a sufficiently low dielectric constant so as to allow said antimicrobial agent to form a chain-like structure to create an initial dose of antimicrobial action upon first use by allowing antimicrobial ions on a surface of said composition to dissolve, said chain-like structure providing a pathway in said binder to allow interior antimicrobial ions in said composition to come to said surface of said composition to provide subsequent doses of antimicrobial action.

8. The antimicrobial composition for coating articles of claim 7 wherein said binder consists essentially of acrylonitrile-butadiene-styrene copolymers.

9. The antimicrobial composition for coating articles of claim 7 wherein said binder consists essentially of a mixture of 35 to 65 percent by weight of acrylonitrile-butadiene-styrene copolymers and 35 to 65 percent by weight of polyvinyl chloride.

10. The antimicrobial composition for coating articles of claim 9 wherein said zone of inhibition forms, in 24 hours, a solution of at least $10^{-6}$ molar concentration of silver ion concentration in a stagnant film of urine in contact with said surface.

11. A catheter adapter for use in indwelling urethral catheterization including an antimicrobial coating thereon; said antimicrobial coating comprising a binder and an antimicrobial metal compound;
- said binder being from 30–99.85% by weight of the coating and selected from a group consisting essentially of acrylonitrile-butadiene-styrene copolymers, polyvinyl chloride, polyesters, polyurethanes of mixtures thereof;
- said antimicrobial metal compound being 0.15–70% by weight o the coating selected from the group consisting of compounds of antimicrobial metals and mixtures thereof that are physiologically compatible with human tissue, said binder having a sufficiently low dielectric constant so as to allow said antimicrobial agent to form a chain-like structure to create an initial dose of antimicrobial action upon first use by allowing antimicrobial ions on a surface of said composition to dissolve, said chain-like structure providing a pathway in said binder to allow interior antimicrobial ions in said composition to come to said surface of said composition to provide subsequent doses of antimicrobial action.

12. The catheter adapter of claim 11 wherein said binder is of a high dielectric constant to provide discreetly dissolved particles on the surface to provide an initial high dose of antimicrobial metal compound.

13. The catheter adapter of claim 12 wherein said antimicrobial metal compound is of large particle size and is discreetly dissolved in the surface of the binder; and, said antimicrobial composition is selected from the group consisting of oxides and salts of silver and gold.

14. The catheter adapter of claim 13 wherein said antimicrobial composition forms a zone of inhibition which prevents and kills bacteria growth thereabout.

15. A silicone rubber foley catheter for use in indwelling urethral catheterization including an antimicrobial coating thereon;
- said antimicrobial coating thereon;
- said antimicrobial coating comprising a binder and an antimicrobial metal compound;
- said binder being from 30–99.85% by weight of the coating and selected from a group consisting essentially of alkoxy curing RTV rubber, acidtoxy cured RTV silicone rubber, rubber latexes, and mistures thereof;
- said antimicrobial metal compound being 0.15–70 by weight of the coating selected from the group consisting of compounds of antimicrobial metals and mixtures thereof that are physiologically compatible with human tissue, said binder having a sufficiently low dielectric constant so as to allow said antimicrobial agent to form a chain-like structure to create an initial dose of antimicrobial action upon first use by allowing antimicrobial ions on a surface of said composition to dissolve, said chain-like structure providing a pathway in said binder to allow interior antimicrobial ions in said composition to come to said surface of said composition to provide subsequent doses of antimicrobial action.

16. The silicone rubber foley catheter of claim 7 wherein said antimicrobial metal compound is of small particle size completely dissolved throughout the binder to provide and maintain a desired zone of inhibition in a stagnant film of urine in contact with said catheter for the longest possible period of time.

17. The silicone rubber foley catheter of claim 16 wherein said binder is 95% by weight alkoxy curing RTV rubber and said antimicrobial metal is 5% by weight silver sulfadiazine.

18. The silicone rubber foley catheter of claim 17 wherein said binder is 95-99% by weight alkoxy curing RTV rubber and said antimicrobial metal is 1–5% by weight of silver oxide, forming a smooth, adherent, strong antimicrobial coating capable of being stretched fifty (50) percent and further providing safe effective and long lasting zones of inhibition.

19. A flexible polyvinyl chloride catheter for use in short term indwelling urethral catherterization including an antimicrobial coating thereon;
- said antimicrobial coating comprising a binder and an antimicrobial metal compound;
- said binder being from 30–99.85% by weight of the coating and being of a high dielectric constant; and
- said antimicrobial metal compound being 0.15–70% by weight of the coating and being of small particle size and selected from the group consisting of compounds of antimicrobial metals and mistures thereof that are physiologically compatible with human tissue, said binder having a sufficiently low dielectric constant so as to allow said antimicrobial agent to form a chain-like structure to create an initial dose of antimicrobial action upon first use by allowing antimicrobial ions on a surface of said composition to dissolve, said chain-like structure providing a pathway in said binder to allow interior antimicrobial ions in said composition to come to said surface of said composition to provide subsequent doses of antimicrobial action.

* * * * *